United States Patent [19]

Praeger

[11] Patent Number: 4,676,792
[45] Date of Patent: Jun. 30, 1987

[54] METHOD AND ARTIFICIAL INTRAOCULAR LENS DEVICE FOR THE PHAKIC TREATMENT OF MYOPIA

[76] Inventor: Donald Praeger, 41 Yates Blvd., Poughkeepsie, N.Y. 12601

[21] Appl. No.: 928,871

[22] Filed: Nov. 10, 1986

Related U.S. Application Data

[63] Continuation-in-part of Ser. No. 900,400, Aug. 26, 1986, abandoned.

[51] Int. Cl.$^4$ .................. A61F 2/16; A61B 17/00
[52] U.S. Cl. .................. 623/6; 128/303 R
[58] Field of Search .................. 623/6; 128/303 R

[56] References Cited

U.S. PATENT DOCUMENTS

| 4,435,855 | 3/1984 | Pannu | 623/6 |
| 4,437,194 | 3/1984 | Hahs | 623/6 |
| 4,542,540 | 9/1985 | White | 623/6 |
| 4,581,033 | 4/1986 | Callahan | 623/6 |
| 4,600,003 | 7/1986 | Lopez | 623/6 X |
| 4,619,256 | 10/1986 | Horn | 623/6 X |

FOREIGN PATENT DOCUMENTS

| 7908210 | 6/1981 | Netherlands | 623/6 |
| 2165456A | 4/1986 | United Kingdom | 623/6 |

OTHER PUBLICATIONS

"An Intraocular Lens Carrier" by O. I. Lopez et al., Am Intra-Ocular Implant Soc. Journal, vol. 9, No. 4, Fall 1983, pp. 477-479.
"The Lens, The Copeland Radial Anterior Chamber Lens-UV", Donald L. Praeger, Brochure by Copeland Intra Lenses, Inc., (7 pages) 1982.
"An Ocular Telephoto System Designed to Improve Vision in Macular Disease", Anthony Donn et al., CLAO Journal, V. 12, No. 2, pp. 81-85, (Apr., 1986).
"Optical Problems Following Refractive Surgery", Perry S. Binder, Ophthalmology 93:739-745 (1986).
"Intraocular Lens Data", Robert L. Stamper et al., Dept. of Ophthalmology, Pacific Medical Center, San Francisco (1984); pp. 164-180.
"Intra-Ocular Lenses and Implants", Peter Choyce, pp. 11-15, Chapters 6, 20 and 21 (H. K. Lewis & Co. Ltd. 1964).
"Incidence, Accidents, et. Complications Possibles au Cours de l'Inclusion de Lentilles Plastiques dans la Chanbre Anterieure-Experience Personnelle Basee sur les 132 Premiers Cas", Bull. la Societe Francais D'Ophtalmologie 1957, vol. 70, 233-251.

(List continued on next page.)

Primary Examiner—Ronald L. Frinks
Attorney, Agent, or Firm—Henry R. Lerner; Alfred D'Andrea, Jr.

[57] ABSTRACT

The placing of an artificial intraocular lens device (IOL) in the anterior chamber of the eye (in front of the iris) for treating myopia. The intraocular lens device includes a meniscus style lens which has a plano anterior surface and a concave posterior surface. The edges of the lens are rounded off and the peripheral portion of the lens is considerably thicker than the central portion of the lens. The lens is a minus (negative) refracting lens. The lens is suspended in the anterior chamber by three or four carrying angles or haptics having solid footplates at their ends for anchoring the device in the anatomic angle of the eye. The solid footplates are sized to prevent tissue overgrowth and resulting synechia after placement, additionally facilitating subsequent removal of the lens device from the anterior chamber if necessary. A ridges lens glide is also provided to facilitate insertion of the lens device into the anterior chamber during implantation. This lens device is utilized in the phakic state (the state of the natural lens being retained). With the patient's natural crystalline lens being retained, the natural crystalline lens is located in the posterior chamber behind the iris and the artificial intraocular lens of negative power is located in the anterior chamber in front of the iris. The presence of the phakic state allows for accommodation to occur. The intended age range for applicability of the device is approximately from age 20–50.

32 Claims, 13 Drawing Figures

OTHER PUBLICATIONS

"The Use of Plastic Lenses in the Anterior Chamber: Indications—Techniques—Personal Results", J. Barraquer, *Transactions of the Ophthomology Society of the United Kingdom*, 76:537-52 (1956).

"The Use of Plastic Lenses in the Anterior Chamber", J. Barraquer, *Journal of the International College of Surgeons*, 29 (5 PT.1):629-37 (May, 1958).

"An Intraocular Lens Carrier", O. I. Lopez, et al., *An Intra-Ocular Implant Soc. Journal*, v. 9, pp. 477-479 (Fall 1983).

"Time has Come to Re-Think Phakic IOL Concept", Hirschman, H., Ocular Surgery News, 4/1/86, vol. 4, No. 7, 2 pages.

"Sopportabilia di Lenti Acriliche in Camera Anteriore Nella Afachia e nei Vizi di Refrazione", Ann. Oftal, in Clin. Ocul., 80:75, 1954 (in Italian Journal of Ophthalmology), pp. 1-8.

"Lentes Plasticos de Camera Anterior", Barraquer, J. M., Estudios C Informaciones Oftalmologicas, vol. 6, No. 15, 1954, Transactions—The Barraquer Institute, Barcelona, Spain, 4 pages.

"Lentilles Plastiques Dan la Cambre Anterieure: Indications, Technique, Experience Personnelle sur Cent Cas", Bull. Soc. Belge Ophthalmol: 114, 503-516, 1956.

"Complications de l'Operation de Streampelli", Strampelli, B., Anne Therapeutique Et Clinique En Ophthalmologique, 1958, vol. 9, 349-370.

"Anterior Chamber Plastic Lenses-Results and Conclusions from Five Years Experience", Dr. J. Barraquer, Barcelona, Trans. Oph. Soc. United Kingdom, 1959, vol. 79, 393-424.

"The Correction of Unilateral Akhakia by Means of all Acrylic Anterior Chamber Implants", D. P. Choyce, F.R.C.S., Presented Louisiana, Miss. Ophthalmologic Soc., Edgewater Park, Miss., 5/15/59, Written Paper, AJO, 1960, vol. 49, 417-439.

"The Use of all Acrylic Anterior Chamber Implants", D. P. Choyce, Trans, Ophthal. Soc. United Kingdom, 1960, vol. 80, 201-218.

"Plastic Lenses for the Anterior Chamber", Baraquer, J., Japanese Journal of Clincial Ophthal., vol. 14, 2006-2007.

"Complicaciones de la Inclusion Segun los Diversos Tipos de Lentes", Barraquer, J., Annales de Instituto Barraquer, 1962, vol. 3, 588-592.

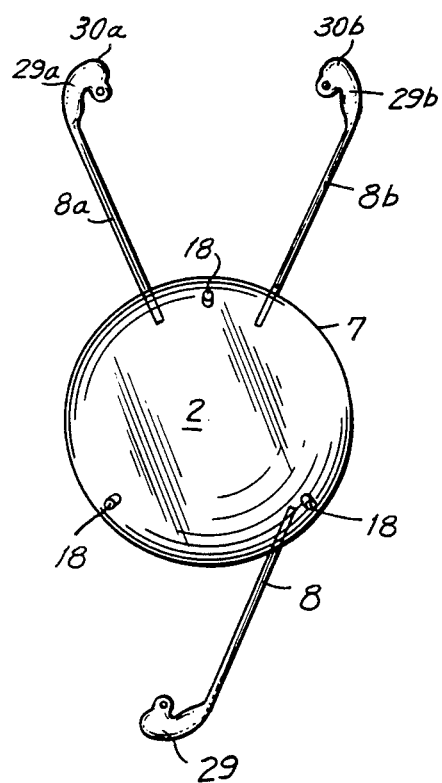
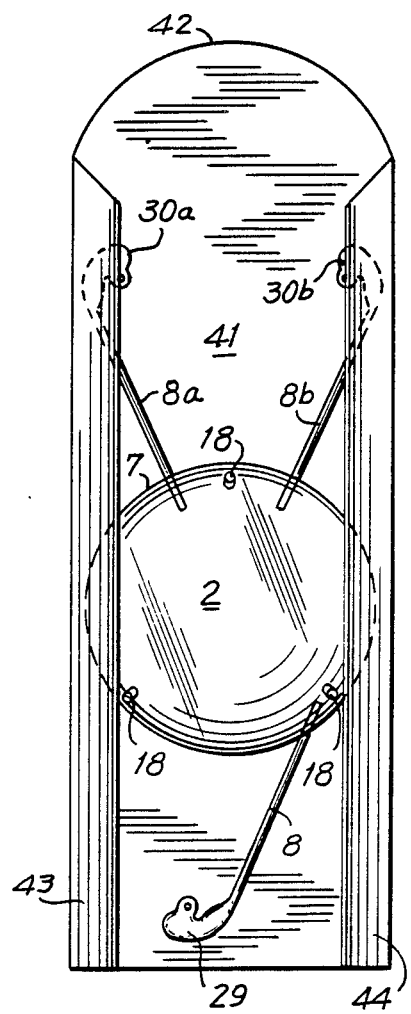

METHOD AND ARTIFICIAL INTRAOCULAR LENS DEVICE FOR THE PHAKIC TREATMENT OF MYOPIA

RELATED APPLICATION

This is a continuation-in-part of my application Ser. No. 900,400 filed Aug. 26, 1986, now abandoned.

BACKGROUND OF THE INVENTION

Presently, the standard technique for the surgical treatment of myopia is a keratorefractive procedure wherein either the shape of the cornea is altered or the refractive index of the cornea is surgically altered. There are many problems associated with this procedure. While many physicians are trained in keratorefaction, relatively few ever perform them and then not often. It thus becomes an intimidating procedure when performed. There are technical difficulties resulting from the microkeratome, the computer and the cryolathe, and many problems in learning to use the cryolathe. Additionally, there are possible complications such as infection, loss of endothelial cells, penetration and perforation. Moreover, in the best of hands, the predictability rate is only about 55 to 65 percent to plus or minus 2 diopters.

Generally, keratorefractive procedures encompass any surgical procedure performed on the cornea, be it with a knife or with laser, which in effect attempts to induce a refractive change. It thereby encompasses radial keratotomy, keratomileusis, keratophakia, epikeratophakia, and polysulfone corneal inlays. It also encompasses the Ruiz procedure for astigmatism or any other type of procedure.

All of the refractive surgical procedures share common optical problems: glare and photophobia, over-correction, under-correction, regular astigmatism, irregular astigmatism, loss of best corrected acuity, fluctuation in visual acuity, loss of progression of effect, and monocular diplopia. These are well known, as reported by Perry Binder in "Optical Problems Following Refractive Surgery", OPTHALMOLOGY (June 1986, v. 93, no. 6).

In sum, even for an experienced surgeon performing a high volume of such procedures, the risks and associated problems are great.

Accordingly, there is a need for a successful phakic myopic implant, where a corrective lens is implanted in the eye without removal of the natural-crystalline lens, thus avoiding the risks associated with keratorefractive procedures.

Implantation of an intraocular lens is a general procedure practiced in one form or another by probably 90 percent of the present ophthalmologists. It is a procedure in which they are experienced. Thus, if a successful lens and method for the phakic treatment of myopia could be developed, the incidence of eyes that would be lost or damaged in treating myopia would clearly be reduced.

Additionally, if a successful lens and method for the phakic treatment of myopia could be developed, the patients would retain their power of accommodation. A 20 year old has an average range of accommodation of about 10 diopters; a 50 year old might have a range of accommodation of about 2.0 diopters. With most accommodation occurring in the anterior lens capsule and with the synkinetic reflex of internal rectus convergence and myosis, a properly vaulted lens would allow for adequate accommodation.

An especially desirable result, were a successful lens and method for the phakic treatment of myopia developed, would be the predictability of success, which would probably be 95 to 98 percent of the time. A common optical complication of all keratorefractive procedures is a 35% to 45% over-correction or under-correction. Moreover, the response time would be only two to three weeks, much less than the response times after keratorefractive procedures. There would be no donor material required and no irreversible incisions in the visual axis.

As a result, it would be highly desirable to develop a lens and method for the phakic treatment of myopia which would work.

The process of implanting an intraocular lens in the anterior chamber of an eye without removing the natural-crystalline lens has been attempted on four previous occasions. The first attempt in the early 1950's was in Italy and employed a solid parabolic-shaped lens which was extremely thick peripherally and centrally. The technique was abandoned after only a few cases. There was no published description of any long term effect. The procedure was a failure owing to the type of lens and technique of implantation employed.

Additional attempts in the mid-1950's were made in Spain and West Germany. These employed a semi-flexible style intraocular lens. These particular lenses were placed into the eye and resulted in a great deal of movement of the lenses after placement. These semi-flexible lenses were made centrally of polymethylmethacrylate and had carrying loops made of supramide and/or nylon. It was not known at that time, but supramide and nylon have proven to be biodegradable substances. As biodegradation progressed, lenses moved and many eyes were lost. These lenses were likewise abandoned. The operative techniques were never revealed and the negative results were never published.

In a fourth attempt in the late 1950's at the phakic treatment of myopia, six cases of implantation in the eye of a solid Choyce Mark-style lens were reported in a 1964 textbook by Mr. Peter Choyce. Choyce stated that the results were fairly satisfactory for binocular myopia, but this procedure was never carried out to any degree after 1964.

The first and fourth attempts employed the same operative technique. Without the benefit of a microscope, a Graffe incision was made in the lateral cornea from approximately 7-11:00 o'clock. A suture was placed through the cornea and retracted nasally. The solid parabolic-shaped lens or the Choyce Mark VIII lens measuring 1.0 mm. greater than the "white-to-white" horizontal eye diameter was then placed into the eye in an "open sky" technique. A peripheral iridectomy was carried out and the eye was sutured.

The phakic treatment of myopia has not been attempted since 1964. It has never been attempted in the U.S.A. The prior existing lenses and techniques of implantation employed were unsuccessful for a wide variety of reasons, including the following:

(A) The lenses were extremely thick and very rigid. There was constant touch to the central and peripheral cornea and many cases of corneal dystrophy resulted although they were not reported in the literature;

(B) The intraocular lens employed could never pass the scrutiny of scanning electron microscopy. Today's lenses are capable of being highly polished, ultrarefined, and tested by scanning electron microscopy before they are sterilized and packaged. In addition, they can be extremely thin with very refined edging and optics. The chemical nature of the plastic is still the same—polymethylmethacrylate;

(C) The only semi-rigid lens employed was a solid polymethylmethacrylate lens with supramide and/or nylon loops. This lens simply did not fit the eye and most often was too short. Those that were of sufficient size ultimately became loose because of the biodegradation of the supramide or nylon as it became encrotched in the anatomic angle of the eye. The action of the blood vessels in the anatomic angle biodegraded the supramide and ultimately the lenses became loose and created havoc within the eye. It is common knowledge in the ophthalmic profession that over 200 eyes were lost in Spain using this lens and procedure.

Finally, modern techniques for the implantation of intraocular lenses in the eye utilize lens glides for assisting the insertion of the lens into the eye. The lens glide is inserted in an incision in the eye. The lens is slid along the lens glide into the eye and positioned. The lens glide is then withdrawn from the eye. Flat lens glides and envelope-type lens glides are used for this purpose. However, flat lens glides merely provide a flat working surface, but beyond this do not facilitate positioning of the lens. Envelope-type lens glides, on the other hand, are inefficient and cumbersome because the lens is slid into the eye through an envelope and accurate positioning of the lens is hampered by continual contact of the lens glide and positioning surgical instrument. An envelope-type lens glide is described by Osvaldo I. Lopez et al. in "An Intraocular Lens Carrier," AM INTRAOCULAR IMPLANT SOCIETY JOURNAL (Fall 1983, v. 9, pp. 477–479).

SUMMARY OF THE INVENTION

An object of the present invention is to provide an improved method of treating myopia.

Another object of the present invention is to provide an improved method of treating myopia which retains the eye's ability to accommodate and which does not alter the cornea or material structure of the eye.

Yet another object of the invention is to provide an intraocular lens device for use in the phakic treatment of myopia which avoids the failures and shortcomings of phakic intraocular lenses used in the past for the surgical correction of myopia.

Still a further object of the present invention is to provide an intraocular lens device for implantation in the eye which is non-biodegradable, which does not produce any light diffraction in the eye and which can subsequently be removed from the eye after implantation if necessary.

Another object of the present invention is to provide an intraocular lens device for implantation into the eye which will correct myopia but which will, in fact, avoid common optical complications of keratorefractive procedures; namely, persistent glare, photophobia, irregular and regular astigmatism, loss of progression of effect and monocular diplopia.

A further object of the present invention is to provide a device which will predictably correct myopia to a degree of 95–98% to the desired result.

Still a further object of the invention is to provide an improved lens glide for insertion of an intraocular lens device into the eye which simplifies insertion of the lens device into the eye and minimizes risks and problems associated therewith.

These and other objects of the present invention are achieved by an artificial, intraocular lens device for placement in the anterior chamber of an eye to treat myopia without removing the natural-crystalline lens of the eye comprising a negative refracting lens having a plano anterior surface and a concave posterior refracting surface, the negative refracting lens having a relatively thin central portion and a relatively thick peripheral portion, the relatively thick peripheral portion having an outer rounded circumferential edge conforming to an internal curve of the cornea of the eye. The intraocular lens device further includes means connected to the negative refracting lens for suspending the negative refracting lens in the anterior chamber of the eye such that the negative refracting lens will never contact the natural-crystalline lens of the eye, means connected to the suspending means for removably anchoring the device in the anterior chamber, and means facilitating insertion and adjustment of position of the device in the anterior chamber.

Preferably, the suspending means comprises three haptics secured to the negative refracting lens at equidistant points around and on the outer, rounded circumferential edge at a vault angle of about 2 to about 3 degrees with respect to the root of the iris and the anchoring means comprises a solid footplate of a flat, scalloped shape connected to each haptic for anchoring the device in the anterior chamber angle while preventing tissue overgrowth and resulting synechia.

In various preferred embodiments, the means facilitating insertion and adjustment of position of the device comprises at least one tab secured to the outer, rounded circumferential edge of the negative refracting lens, each tab having a substantially 0.2 mm diameter hole therein, at least one substantially 0.2 mm diameter hole in the peripheral portion of the lens, each hole having a preferable depth of substantially one-half of the thickness of the peripheral portion of the lens, but not extending completely through the depth of the peripheral portion of the negative refracting lens, or at least one substantially 0.2 mm diameter hole in the outer, rounded circumferential edge of the negative refracting lens.

Further in accordance with the present invention, there is provided a method for treating myopia comprising surgically implanting the novel artificial, intraocular lens device of the present invention in the anterior chamber of an eye and removably anchoring the lens device in the anterior chamber in the anatomic angle of the eye.

In an additional aspect of the present invention, there is provided a ridged lens glide for inserting the novel, artificial, intraocular lens device in the anterior chamber during surgical implantation.

BRIEF DESCRIPTION OF THE DRAWINGS

The intraocular lens device and method of the present invention will now be described with reference to the accompanying drawings, in which:

FIG. 8 is a top plan view of a third embodiment of an intraocular lens device according to the present invention, taken from the perspective of the anterior side of the lens device;

FIG. 12 is a top plan view of the lens glide of FIG. 10, having inserted therein one embodiment of the intraocular lens device of the present invention.

DETAILED DESCRIPTION OF THE PREFERRED EMBODIMENTS

Figure 1:
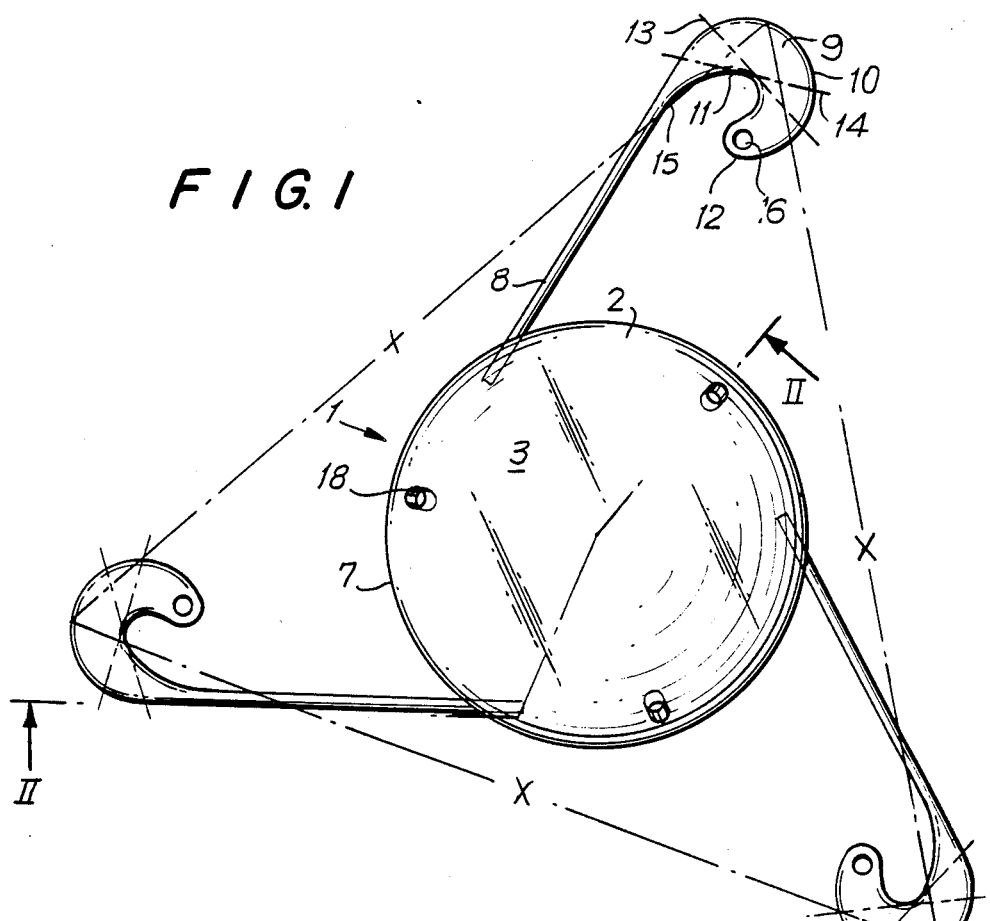
FIG. 1 is a top plan view of a first embodiment of an intraocular lens device according to the present invention, taken from the perspective of the anterior side of the lens device.
Figure 2:
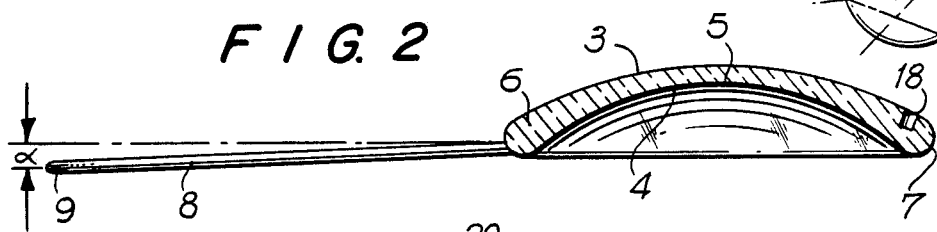
FIG. 2 is a cross-sectional view of the intraocular lens device shown in FIG. 1, taken along the line II—II of FIG. 1.

FIGS. 1 and 2 illustrate a first embodiment of the artificial, intraocular lens device of the present invention.

As shown in these Figures, an artificial, intraocular lens device 1 includes a centrum 2 or lens which constitutes the main body and the entire optical portion of the lens device 1. Centrum 2 comprises a plano anterior surface 3 which is curved slightly at its periphery to conform to the contour of the anterior chamber and cornea of the eye. Centrum 2 further comprises a concave posterior refracting surface 4, containing the entire refracting surface of the centrum, which is rounded at its periphery to conform to the internal curve of the cornea. The minus power is ground in the refracting surface 4.

As shown in FIG. 2, centrum 2 has a relatively thin central portion 5 and a relatively thick peripheral portion 6. Peripheral portion 6 is rounded at an outer circumferential edge 7 to conform to the internal curve of the cornea. This configuration of centrum 2 produces a minus meniscus lens.

Preferably, the lens measures substantially 6.0 to 6.5 mm in diameter and contains an ultraviolet filter which reduces up to 350 to 400 nm of ultraviolet light, generally acknowledged to be a desirable characteristic. It has been found that the pupils of myopes dilate to from 5.5 to 6.0 mm. Accordingly, a 6.5 mm diameter is especially preferred to prevent any overlap of the pupil and centrum 2, which might otherwise occur if the pupil were larger than the centrum 2.

The thickness of the relatively thin portion 5 depends upon the radius of curvature of the phakic lens 2 which is an optical property depending upon the desired dioptric power of the lens which in turn depends upon the degree of myopic disability of the eye to be treated. Ideally, a patient's refraction would be adjusted to either an emmetropic state or perhaps to a slight myopic state of about −1.00 diopter. Using a nomogram, it is possible to predict this using a keratometric reading and excellent phakic refraction at the distance position with careful measurement of the vertex. A-scan for anterior chamber depth would measure the critical depth of the chamber both at distance and at near while accommodating. From this, anterior chamber diminution and the necessary thickness for the central portion is calculated.

Centrum 2 is made of a solid, optical, non-biodegradable material, preferably optical ground polymethylmethacrylate (PMMA), and is either lathe-cut or injection molded. Other materials, such as polysulfone, which have a higher index of refraction than PMMA and are consequently thinner, may be used.

The artificial, intraocular lens device 1 of FIGS. 1 and 2 further includes three carrying loops or haptics 8 secured equidistantly around and to the outer circumferential edge 7 of centrum 2. Accordingly, haptics 8 are spaced 120 degrees apart around outer circumferential edge 7.

A solid footplate 9 is integrally formed on the end of each haptic 8. Solid footplate 9 has a scalloped-type configuration, with a curved surface 10 which contacts the anatomic anterior chamber angle essentially continuously from the haptic 8, and a scalloped surface 11 extending from junction 15 of footplate 9 and haptic 8 to the curved surface 10 at an apex 12.

The solid footplates 9 serve to removably anchor the lens device 1 in the anterior chamber, as will be described more fully hereinafter. The footplates 9 are inserted into the anatomic angle of the eye, a technique which will be described fully hereinbelow.

Another purpose of solid footplates 9 is to prevent tissue overgrowth at the ends of the haptics 8 after the lens device is implanted and secured in the anterior chamber. To achieve this result, solid footplate 9 preferably measures about 1.0 mm by about 1.0 mm horizontally and vertically, i.e., 1.0 mm by 1.0 mm as shown by dotted lines 13 and 14 in FIG. 1.

A small positioning hole 16 is located in each solid footplate 9, preferably at the furthest point in the footplate from junction 15 along the surface of the footplate which is closest to the centrum 2 when the lens device 1 is placed in the anterior chamber of the eye. Positioning hole 16 facilitates adjustment of the solid footplate during insertion of the lens device if the footplate should engage the iris. An appropriately-sized surgical instrument is inserted into the positioning hole 16 and the footplate 9 disengaged from the iris and guided into the anatomic angle. Preferably, positioning hole 16 has a diameter of approximately 0.2 mm. Positioning hole 16 is far enough away from the contact point of footplate 9 in the anatomic angle to prevent any tissue growth and yet permits successful manipulation of the footplate 9, if necessary.

Figure 3:
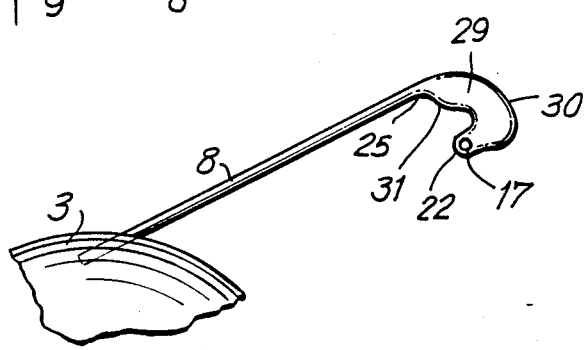
FIG. 3 is a perspective plan view of one preferred form of haptic and solid footplate for use in the intraocular lens device of the present invention.

As an alternative to footplate 9 and positioning hole 16, and as shown in FIG. 3, a solid footplate 29 may be provided with an integral tab positioning hole 17, which functions in the same manner as positioning hole 16. The diameter of tab positioning hole 17 is preferably about 0.2 mm. Solid footplate 29 has a scalloped-type configuration, with a curved surface 30 which contacts the anatomic anterior chamber angle essentially continuously from haptic 8, and a scalloped surface 31 extending from junction 25 of footplate 29 and haptic 8 to the curved surface 30 at an apex 22.

Solid footplates 9 and 29 prevent the overgrowth of tissue on the ends of haptics 8, thus precluding the development of adhesions (synechia) at the point of contact of the intraocular lens device 1 and the point of fixation thereof in the anatomic angle of the eye. Moreover, solid footplates 9 and 29 are much less prone to catch on the iris and get entangled in other structures of the eye than prior devices for fixing intraocular lenses in the anatomic angle of the eye.

As shown in FIG. 1, the bow-to-bow cord measurement x between the outer apex of each footplate 9 is at least substantially 14.0 mm, and most preferably substantially 14.0 mm, thus forming an imaginary equilateral triangle with equal sides of substantially 14.0 mm. This is critically different from various prior art lens devices, such as the Copeland anterior chamber high plus lens used for the surgical correction of aphakia following the removal of a cataract, which measures substantially 13.75 mm and is inadequate to adapt itself to a moderate to large myopic eye. The intraocular lens device of the present invention can adapt itself to the full range of myopic eyes.

As shown in FIG. 2, the haptics 8 form a vault angle with respect to centrum 2 to prevent contact of the natural-crystalline lens and iris of the eye with the intraocular lens device of the present invention after implantation. Preferably, vault angle ranges from about 2 to about 3 degrees, most preferably 3 degrees. This provides an anterior chamber fixation, having the least amount of contact while simultaneously providing the broadest support without touched iris and/or crystalline lens, which allows for anterior chamber shallowing during the process of accommodation.

One of the advantages of the intraocular lens device of the present invention is that, since the lens device is implanted without removing the natural-crystalline lens from the eye, the ability of the eye to accommodate is retained. During the course of accommodation, the natural-crystalline lens increases slightly in anterior/posterior diameter, i.e., it thickens from front to back. It is acknowledged that most accommodation occurs in the anterior lens surface. A normal crystalline lens is protected from herniation into the anterior chamber by simultaneous miosis during accommodation. Accordingly, the artificial, intraocular lens device of the present invention must be located in the anterior chamber of the eye in a vaulted position away from the natural-crystalline lens to prevent contact therebetween during accommodation.

Figure 4:
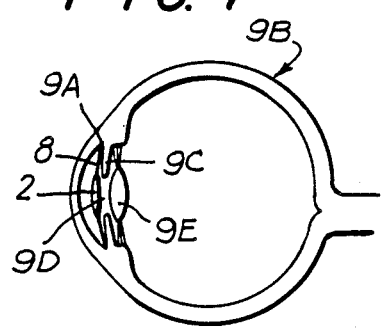
FIG. 4 is a side cross-sectional view of an eye containing an implanted intraocular lens device in accordance with the invention.

As shown in FIG. 4, a vaulted position means that the centrum 2 of the lens device is fixated by solid footplates 9 in three areas of contact in the anatomic angle 9A of the eye 9B. It is then vaulted by the haptics 8 off of the iris 9C and away from the pupil 9D, occupying a point slightly off the iris 9C but well away from the corneal endothelium, as shown in FIG. 4, and as well known in the art. The natural-crystalline lens is labelled 9E.

Figure 5:
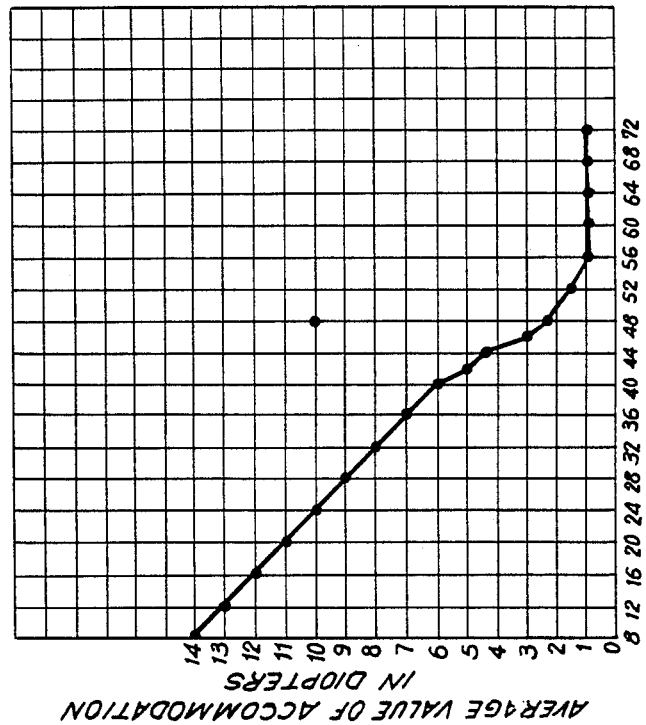
FIG. 5 is a graph of the ability of an eye to accommodate, taken as an average value and measured in diopters, versus age.

FIG. 5 is a graph of the ability to accommodate, taken as an average value and measured in diopters, versus age. As can be seen from FIG. 5, the ability to accommodate diminishes with age. Accordingly, the vault angle necessary to prevent contact between the natural and intraocular lenses decreases with age. For patients under the age of 30, with substantial ability to accommodate, it is essential to use a vault angle of approximately 2.5 to about 3 degrees. If a patient is over 30, a 2 degree vault angle is satisfactory to insure no contact. With a 2.5 to 3 degree vault angle and known miosis under age 30, there is no possibility of contact between the natural-crystalline lens and intraocular lens device of the present invention.

Haptics 8 and solid footplates 9 are made of a non-optical, non-biodegradable material, preferably non-optical polymethylmethacrylate (PMMA). Accordingly, the optic or centrum remains centered even when substantial compression forces are applied at various angles, owing to the semi-flexible nature of the PMMA haptic.

The artificial, intraocular lens device 1 additionally includes means facilitating insertion and adjustment of position of the device in the anterior chamber. Preferably, this means comprises at least one small positioning partial hole in the centrum 2, at least one tab with a small positioning hole on the outer circumferential edge 7, or at least one small positioning partial hole in the outer circumferential edge 7.

In the embodiment shown in FIGS. 1 and 2, one especially preferred form for the insertion and adjustment means is illustrated. Specifically, centrum 2 contains three small positioning holes 18 located in the relatively thick peripheral portion 6 of centrum 2. Holes 18 range from about 0.15 to about 0.25 mm in diameter, or are small enough to receive the tip of a bent 27 gauge needle, and are preferably located approximately 120 degrees apart. The holes 18 do not extend completely through peripheral portion 6, and preferably have a depth into peripheral portion 6 of substantially one-half of the thickness of peripheral portion 6, from the anterior surface 3 towards the posterior surface 4.

Positioning holes have been used in the past. However, recipients of intraocular lenses have complained of annoying diffraction of light and light scattering. It has been discovered that the cause of this light diffraction and scattering is due to excessively large positioning holes and through-holes in the lens. Accordingly, in the present invention, light diffraction and scattering are eliminated by positioning holes which are large enough to accommodate a small positioning device, yet which only extend partially through the peripheral portion of the lens, in effect being covered on the posterior surface by optical PMMA. They are also small enough to further eliminate light diffraction and scattering.

Positioning holes 18 are not limited in use to the intraocular lens device of the present invention and can be employed with any intraocular lens device requiring insertion and adjustment of position in the eye.

Figure 6:
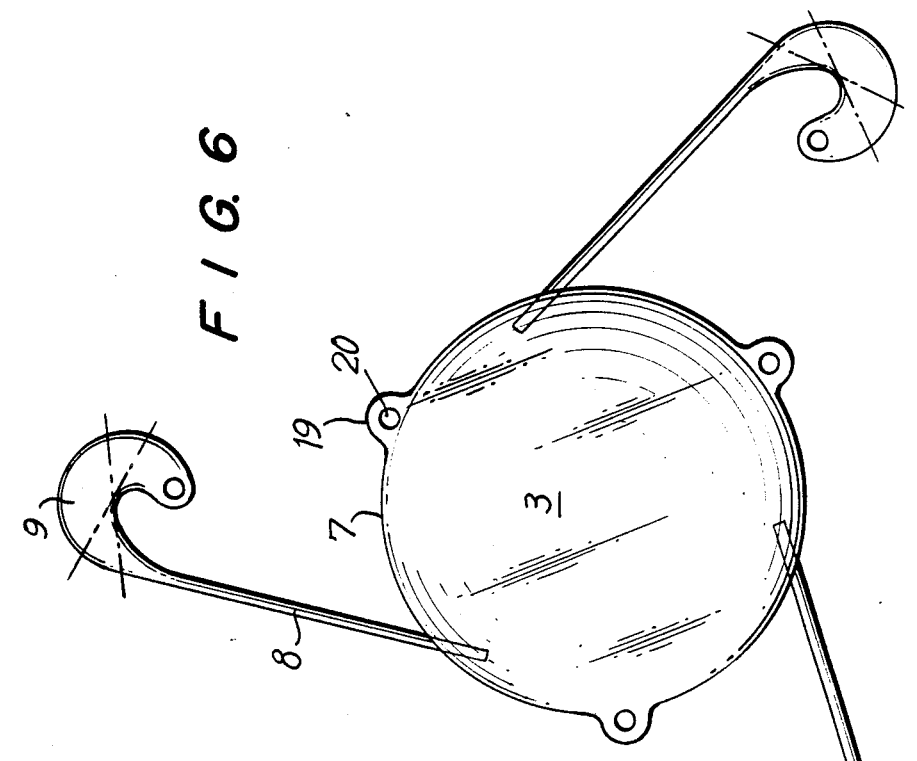
FIG. 6 is a top plan view of a second embodiment of an intraocular lens device according to the invention, taken from the perspective of the anterior side of the lens device.

Alternatively, in another embodiment of the present invention, the problem of light scattering and diffraction is overcome by providing a plurality of tabs 19 on the outer, rounded circumferential edge 7 of centrum 2, as shown in FIG. 6. Each tab 19 is made of a non-optical and non-biodegradable material, preferably polymethylmethacrylate (PMMA), measures approximately 0.6 mm by 0.6 mm to about 0.75 mm by 0.75 mm in its horizontal and vertical dimensions, and contains a hole 20 therein measuring approximately 0.15 to about 0.2 mm in diameter to assist in holding and positioning of the lens device 1 in the anterior chamber. The tabs 19 are preferably located 120 degrees apart around the circumferential edge of centrum 2 and have a parabolic outer contour.

Figure 7:
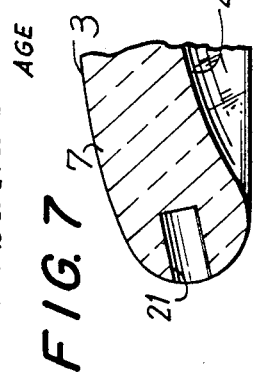
FIG. 7 is an enlarged cross-section view of the peripheral portion of the lens of the intraocular lens device according to the invention.

In another embodiment of the present invention, the problem of light diffraction and scattering is eliminated by providing a plurality of small positioning holes in the outer, rounded circumferential edge 7 of the centrum 2, as shown in FIG. 7. Specifically, holes 21 measure approximately 0.15 to about 0.2 mm in diameter and have a depth into the circumferential edge 7 of about 0.4 to about 0.5 mm. Preferably, there are three small positioning holes 21 spaced equidistantly around outer circumferential edge 7. If the diameter of positioning hole 21 is not more than 0.15 mm, the lens device can be held with a specially-designed holder such as a small microbayonet holder.

The purpose of the small positioning holes 18, the tabs 19, and the small positioning holes 21 is to provide something in the lens device to secure a surgical device to for holding the lens device and placing it in the eye, for positioning the lens and additionally, if necessary, for assisting the surgeon in moving the lens device during interoperative maneuvers. These purposes are achieved without resulting in an implanted lens device which subsequently scatters and diffracts light in the user's eye.

While it is preferred that the intraocular lens device of the present invention comprise three haptics and solid footplates spaced equidistantly around the circumferential edge of the centrum of the lens device, such is not essential to the practice of the invention, and modifications may be made without departing from the spirit and scope of the invention.

For example, as shown in FIG. 8, which illustrates another embodiment of the present invention, solid footplates similar to the previously-described haptics 8 and solid footplates 29 are employed, but the haptics are not spaced equidistantly around the centrum 2. Specifically, two haptics 8a and 8b are spaced less than 120° from each other and are oriented such that their respective curved surfaces 30a and 30b of solid footplates 29a and 29b face each other. Additionally, three positioning holes 18 are employed, but they are not spaced equidistantly around the centrum 2.

Figure 9:
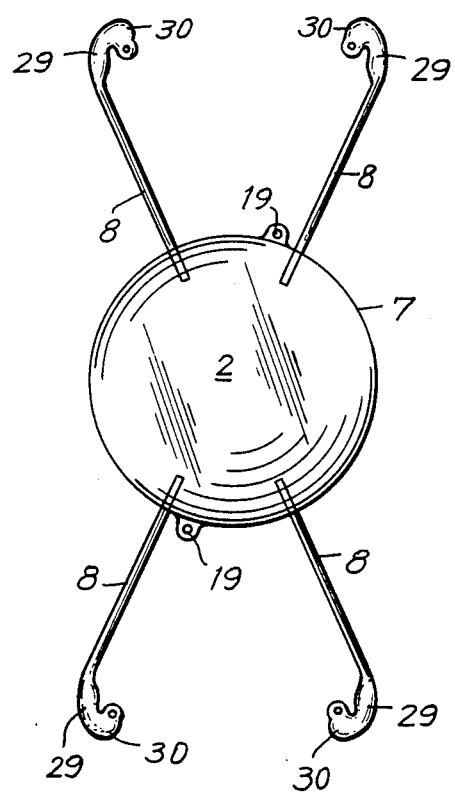
FIG. 9 is a top plan view of a fourth embodiment of an intraocular lens device according to the present invention, taken from the perspective of the anterior side of the lens device.

Similarly, as shown in FIG. 9, illustrating yet another embodiment of the present invention, there are provided four haptics 8 and four solid footplates 29. Haptics 8 are positioned around the circumferential edge 7 of centrum 2 approximately 90° apart. Moreover, haptics 8 are grouped into two pairs, the two haptics 8 in each pair being oriented such that the respective curved surfaces 30 of solid footplates 29 face each other. Finally, two positioning tabs 19 are employed. Haptics 8 may be spaced other than 90° apart.

In the embodiments shown in FIGS. 8 and 9, one or more positioning holes 18, tabs 19, and/or positioning holes 21, as described in previous embodiments, may be provided for positioning and moving the lens device during interoperative maneuvers without causing light diffraction and scattering.

As will be described more fully hereinbelow, the embodiments illustrated in FIGS. 8 and 9 are especially suited for use with a novel ridged lens glide of the present invention.

The technique for implanting the intraocular lens device of the present invention will now be described. The eye is made soft with an osmodiuretic and a local or general anesthesia is administered. Pilocarpine is placed into the eye in order to facilitate miosis, making the pupil small. A giant operating microscope is used throughout the procedure. Careful gonioscopic examination of the chamber angle is performed a few days prior to surgery and anatomic landmarks of the angle are mapped out. The area near the incision is cauterized and all bleeding vessels are cauterized. A knife needle tract is established at the 2:00 o'clock position into clear cornea. A half-thickness limbal incision is made 3-4 mm. from the limbus and then carried down to the limbus. The anterior chamber is irrigated with Miochol solution to again make the pupil extremely small. A visco elastic material such as Viscoat or Healon is injected into the anterior chamber, deepening the chamber. A lens glide, basically a sliding board on which the lens will pass down, is then placed into the anterior chamber. The intraocular lens device is then grasped with a small toothed forcep. It is placed in under the viscoat elastic material on the lens glide. The inferior haptic is delivered down to the 6:00 o'clock position and, by rotating the carrying loops, the 2 lower loops are placed into position. The third loop is then placed into direct observation using a curved toothed forcep. The lens glide is removed. The purpose of the lens glide is to protect the natural phakic crystalline lens. The incision is closed. The Healon or Viscoat may be left in the eye. At the completion of the procedure a small peripheral iridectomy is done near the incision. Conjunctiva is reposited and held with cautery.

The visco elastic material is a thick, inert biologic substance that keeps the delicate corneal endothelium away from the lens. This medication reabsorbs after the surgery in a day or two and, with the eye sutured, there can be virtually no contact between the lens loop bodies or footplates and the cornea or iris.

A suitable technique for implantation is the technique used for implanting the Copeland anterior chamber high plus lens for the surgical correction of aphakia, originated by the present inventor as disclosed in the brochure "The Lens. The Copeland Radial Anterior Chamber Lens-UV.", available from Copeland Intra Lenses, Inc. and incorporated herein by reference.

FIGS. 10 through 13 illustrate a novel ridged lens glide especially suitable for use in inserting the artificial, intraocular device of the present invention in the anterior chamber of the eye.

As shown in FIGS. 10 to 13, the ridged lens glide, indicated generally at 40, includes a flat base member 41 having a smooth front curved edge 42. Base 41 supports the centrum 2 of the intraocular lens device thereon. A pair of ridges 43 and 44 extend towards each other from the longitudinal side edges of base portion 41 and are disposed such that they extend inwardly of base portion 41 and form channels 45 and 46 with base portion 41. Ridges 43 and 44 are of a width sufficient to removably receive the footplates 29 of the intraocular lens device in the channels 45 and 46, preferably about 0.5 mm. Ridges 43 and 44 terminate in spaced relation to each other, thereby leaving a central longitudinal portion of base member 41 visible and accessible, so as to permit direct manipulation of the intraocular lens device in the lens glide, especially direct manipulation of positioning holes or positioning tabs in the intraocular lens device. Accordingly, the intraocular lens device removably received in the lens glide may be contacted without contacting the lens glide.

The width of the base member 41 of lens glide 40 is slightly greater than the width of the centrum of the intraocular lens device inserted in the lens glide and is thus chosen according to a given lens device. This permits unhampered but controlled insertion and removal of an intraocular lens device to and from lens glide 40. For example, if the diameter of the centrum of the intraocular lens device to be removably received in the lens glide 40 is approximately 6.0 mm, a suitable and preferred width for the base member 41 of lens glide 40 is approximately 6.5 mm.

Lens glide 40 is made of a transparent material, preferably polypropylene. Other suitable lens glide materials are well-known in the art.

Figure 13:
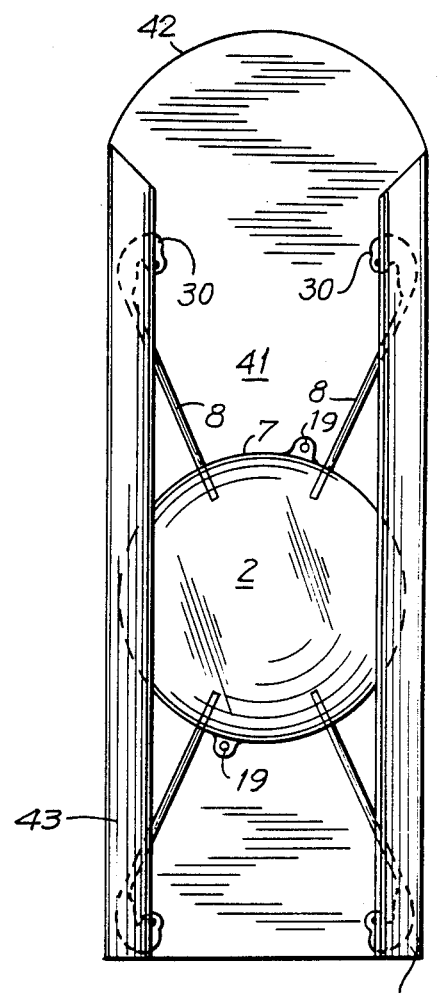
FIG. 13 is a top plan view of the lens glide of FIG. 10, having inserted therein another embodiment of the intraocular lens device of the present invention.
Figure 10:
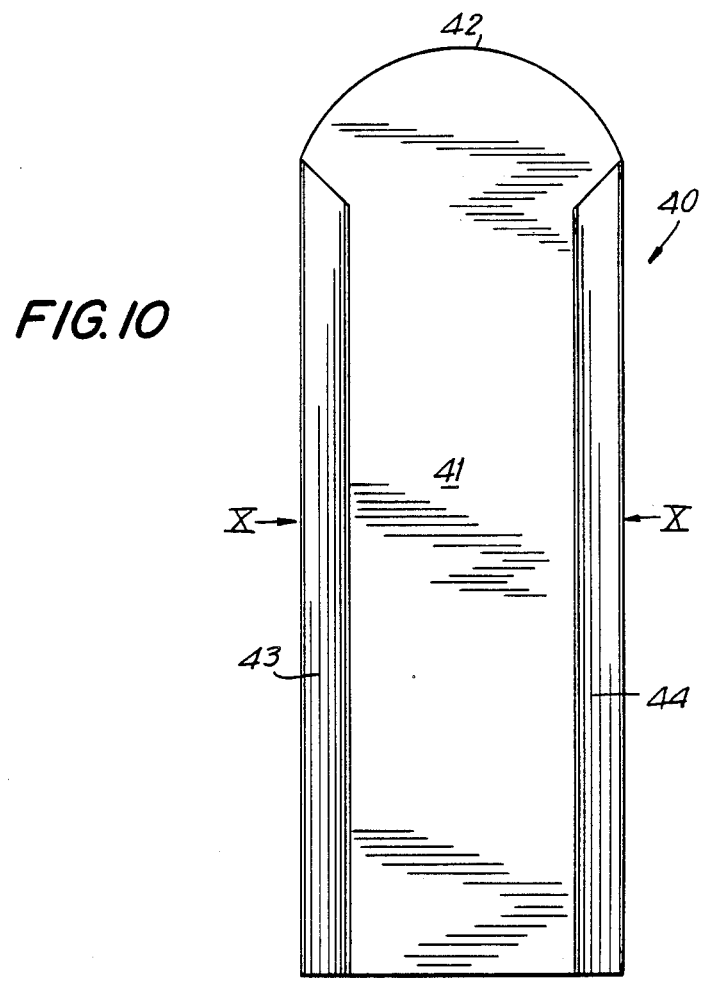
FIG. 10 is a top plan view of the ridged lens glide of the present invention.
Figure 11:
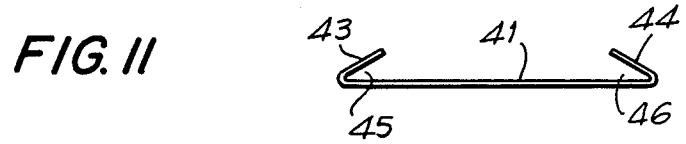
FIG. 11 is a cross-sectional view of the ridged lens glide shown in FIG. 10, taken along the line X—X of FIG. 10.

FIGS. 12 and 13 illustrate, respectively, the intraocular lens devices of FIGS. 8 and 9 removably secured in lens glide 40.

To insert the intraocular lens device into lens glide 40, the front haptics of the lens device, made of a flexible material such as PMMA, are squeezed together and the intraocular lens device is slid into the lens glide. When the front haptics are released, the footplates engage the channels 45 and 46 and the lens device is removably received in the lens glide 40. Centrum 2 rests on the base member 41 of the lens glide 40. A slight gap exists on either side of the centrum 2 between circumferential edge 7 and the outer edges of the base member 41 to facilitate movement of the lens device through the lens glide. Positioning holes 18 and positioning tabs 19 are positioned around centrum 2 such that they do not engage and are not covered by ridges 43 and 44, so that a surgical instrument can be inserted therein without contacting the lens glide at all.

To insert the intraocular lens device into the eye, the general technique described above is employed, with the following modifications. Specifically, the lens glide 40 and removably received lens device are inserted together through the limbal incision into the anterior chamber of the eye. The lens device is then held in place, e.g., by a small toothed forcep inserted through a small, separate side portal incision in the eye and into a rearward positioning hole 18 or positioning tab 19 of the lens device. The lens glide 40 is then manually slid out of the eye while the lens device is held in place. As the lens device slides out of the lens glide being slid out of the eye, the front haptics of the lens device, e.g., haptics 8a and 8b in FIG. 8, which have been held inwardly by the channels 45 and 46 of lens glide 40, spring outwardly and automatically into the anatomic angle of the eye. When the lens glide 40 is completely removed from the eye, the remaining haptic or haptics of the lens device are positioned manually into the anatomic angle with a small toothed forcep inserted through the limbal incision.

While the lens glide 40 has been illustrated with the intraocular lens device of the present invention, it will be appreciated that lens glide 40 can be used for smoothly inserting any intraocular lens device into the anterior or posterior chamber of the eye.

The lens glide of the present invention provides for the simplified insertion of an intraocular lens device into the anterior or posterior chamber of the eye while eliminating problems associated with prior lens glides. For example, the surgical technique is simplified since the front haptics of a lens device are automatically positioned in the anatomic angle when the lens glide is removed. Moreover, there is no possibility of the lens device sliding off the lens glide accidentally and prematurely, as is the case with flat lens glides. Additionally, direct manipulation of the lens device is possible without contacting the lens glide, thus insuring accurate and direct manipulation, which is not possible with envelope-type lens glides. Moreover, the lens glide reduces the occurrence of surgical instrument insertion through the limbal incision, since only the rear haptics need to be manually positioned in the anatomic angle and the lens device can be held and positioned with a surgical instrument inserted through a separate and much smaller side portal incision. Finally, since the lens device can be held in place with a surgical instrument through the small side portal incision, the lens glide can also be easily removed from the limbal incision while the lens device is held in place with the instrument, without either having to remove the surgical instrument or remove the lens glide over the instrument, as is the case with envelope-type lens glides. In sum, the accuracy and efficiency of lens insertion and placement is remarkably improved with the ridged lens glide of the present invention.

It will thus be appreciated that, in accordance with the invention, there is provided an artificial, intraocular lens device and method of treating myopia or nearsightedness which does not require removal of the natural-crystalline lens of the eye, which can correct myopia from a dioptic power of $-3.00$ to $-4.00$ up to $-30.00$ to $-35.00$ and which does not surgically alter the cornea or any material structure of the eye. It allows the patient to retain his or her own natural lens while adding a negative refracting lens to treat the nearsightedness, an artificial lens which can subsequently be removed from the anterior chamber of the eye, if necessary. No sizing is necessary, since a lens material such as polymethylmethacrylate loses memory and will accommodate itself to any circular diameter from 10.5 to 14.00 mm. The lens is non-biodegradable and biologically inert.

With the solid footplates there is no chance for overgrowth or synechia. The vault allows for the crystalline lens to expand anteriorly during the process of accommodation without fear of touch. It is important to know that the accommodative reflex includes miosis which is a further protection to the patient's crystalline lens.

Accordingly, the present invention provides an artificial intraocular lens to treat myopia in people who are unable to wear contact lenses or glasses, who have particular problems with magnification and who are generally unsuited for conventional spectacles or contact lenses. It is ideally suited to a healthy eye wherein there is no evidence of long-term glaucoma, cataract, retinal detachment, or pre-existing corneal disease.

Finally, the present invention provides a lens glide for insertion of an intraocular lens device into the eye which provides accurate and simplified insertion of the lens device and eliminates problems associated with flat and envelope-type lens glides.

I will be understood that the specification and preferred embodiments are illustrative but not limitative of the present invention. Other embodiments within the spirit and scope of the invention will suggest themselves to those skilled in the art.

Having thus described my invention, what I claim and desire to secure by Letters Patent is:

1. An artificial, intraocular lens device for placement in an anterior chamber of an eye for treating myopia without removing a natural-crystalline lens of the eye, comprising a negative refracting lens having a plano anterior surface and a concave posterior refracting surface, the negative refracting lens comprising a relatively thin central portion and a relatively thick peripheral portion, said relatively thick peripheral portion having an outer, rounded circumferential edge conforming to an internal curve of a cornea of the eye; and means for anchoring the negative refracting lens in the anterior chamber of the eye.

2. A lens device according to claim 1, further comprising means for suspending the negative refracting lens in the anterior chamber of the eye.

3. A lens device according to claim 1, further comprising means facilitating insertion and adjustment of position of the device in the anterior chamber.

4. A lens device according to claim 1, wherein the lens comprises polymethylmethacrylate.

5. A lens device according to claim 1, wherein the lens has a diameter of substantially 6.5 mm.

6. A lens device according to claim 1, wherein the means for anchoring the lens in the anterior chamber are removable.

7. A lens device according to claim 2, wherein the means for suspending the negative refracting lens in the anterior chamber comprises three haptics secured to the outer rounded circumferential edge, and wherein the means for anchoring the lens in the anterior chamber comprises a solid footplate connected to each haptic for removably anchoring the lens in the anterior chamber and preventing tissue overgrowth.

8. A lens device according to claim 7, wherein each solid footplate comprises a scalloped structure formed by a curved edge and a scalloped edge, said curved edge extending continuously from said haptic.

9. A lens device according to claim 8, wherein each footplate further comprises means defining a hole in the footplate for facilitating positioning and adjustment of the footplate during placement.

10. A lens device according to claim 8, further comprising a tab connected to each footplate and means defining a hole in the tab for facilitating positioning and adjustment of the footplate during placement.

11. A lens device according to claim 7, wherein said haptics suspend the lens in the anterior chamber of the eye at a vault angle of about 2 to about 3 degrees with respect to the root of the iris to prevent contact of the negative refracting lens with the natural-crystalline lens.

12. A lens device according to claim 7, wherein the haptics are secured to the outer rounded circumferential edge at equidistant points around the outer rounded circumferential edge.

13. A lens device according to claim 8, wherein two adjacent solid footplates face each other.

14. A lens device according to claim 3, wherein the means facilitating insertion and adjustment of position of the device in the anterior chamber comprises at least one tab secured to the outer, rounded circumferential edge of the negative refracting lens, each tab having means defining a substantially 0.2 mm diameter hole therein.

15. A lens device according to claim 3, wherein the means facilitating insertion and adjustment of position of the device in the anterior chamber comprises means defining at least one hole extending only partially into the thickness of the peripheral portion of the negative refracting lens, each said hole having a diameter ranging from about 0.15 to about 0.25 mm and a depth less than the thickness of the peripheral portion, whereby to reduce light diffraction and scattering.

16. A lens device according to claim 15, wherein each hole has a diameter of substantially 0.2 mm and a depth of substantially one-half the thickness of the peripheral portion.

17. A lens device according to claim 3, wherein the means facilitating insertion and adjustment of position of the device in the anterior chamber comprises means defining at least one substantially 0.2 mm diameter hole in the outer, rounded circumferential edge of the negative refracting lens.

18. A lens device according to claim 1, wherein the negative refracting lens further comprises an ultraviolet filter capable of absorbing up to about 350 to 400 nm of ultraviolet light.

19. A lens device according to claim 2, wherein the means for suspending the negative refracting lens in the anterior chamber comprises four haptics secured to the outer rounded circumferential edge and, wherein the means for anchoring the lens in the anterior chamber comprises a solid footplate connected to each haptic for removably anchoring the lens in the anterior chamber and preventing tissue overgrowth.

20. A lens device according to claim 19, wherein the haptics are secured to the outer rounded circumferential edge at equidistant points around the outer rounded circumferential edge.

21. A lens device according to claim 19, wherein each solid footplate comprises a scalloped structure formed by a curved edge and a scalloped edge, said curved edge extending continuously from said haptic.

22. A lens device according to claim 21, wherein a first and second of said solid footplates face each other.

23. A lens device according to claim 22, wherein a third and fourth of said solid footplates face each other.

24. An artificial, intraocular lens device for placement in an anterior chamber of an eye for treating myopia without removing a natural-crystalline lens of the eye, comprising a negative refracting lens having a plano anterior surface and a concave posterior refracting surface, the negative refracting lens comprising a relatively thin central portion and a relatively thick peripheral portion, the relatively thick peripheral portion having an outer, rounded circumferential edge conforming to an internal curve of a cornea of the eye;

means connected to the negative refracting lens for suspending the negative refracting lens in the anterior chamber at a vault angle of about 2 to about 3 degrees with respect to the root of the iris of the eye to prevent contact of the negative refracting lens with the natural-crystalline lens, said means for suspending the negative refracting lens comprising three haptics secured to the outer, rounded circumferential edge at equidistant points around the outer, rounded circumferential edge;

means connected to the means for suspending the negative refracting lens for anchoring the device in the anterior chamber, said means for anchoring the device comprising a solid scallop-shaped footplate connected to each haptic for anchoring the device in the anterior chamber while preventing tissue overgrowth and resulting synechia; and means facilitating insertion and adjustment of position of the device in the anterior chamber.

25. A lens device according to claim 24, wherein the means facilitating insertion and adjustment of position of the device in the anterior chamber comprises at least one tab secured to the outer, rounded circumferential edge of the negative refracting lens, each tab having means defining a substantially 0.2 mm diameter hole therein.

26. A lens device according to claim 24, wherein the means facilitating insertion and adjustment of position of the device in the anterior chamber comprises means defining at least one hole extending partially through the thickness of the peripheral portion of the negative refracting lens, each said hole having a diameter of substantially 0.2 mm and a depth of substantially one-half the thickness of the peripheral portion.

27. A lens device according to claim 24, wherein the means facilitating insertion and adjustment of position of the device in the anterior chamber comprises means defining at least one substantially 0.2 mm diameter hole in the outer, rounded circumferential edge of the negative refracting lens.

28. A method of treating myopia without removing a natural-crystalline lens from an eye, comprising surgically implanting in an anterior chamber of the eye an artificial, intraocular lens comprising a negative refractive lens having a plano anterior surface, a concave posterior refracting surface, a relatively thin central portion and a relatively thick peripheral portion, the relatively thick peripheral portion having an outer, rounded circumferential edge conforming to an internal curve of a cornea of the eye; and anchoring the lens in the anterior chamber in an anatomic angle of the eye.

29. A method according to claim 28, further comprising suspending the lens in the anterior chamber such that the lens will never contact the natural-crystalline lens of the eye.

30. A method according to claim 28, wherein the lens is removably anchored in the anatomic angle of the eye.

31. A method according to claim 30, wherein the lens is removably anchored in the anatomic angle of the eye while preventing subsequent tissue overgrowth once the lens is anchored.

32. A method according to claim 28, further comprising facilitating insertion and adjustment of the lens in the anterior chamber without creating light diffraction and scattering through the lens.

* * * * *